United States Patent
Yamanouchi (10) Patent No.: US 12,409,303 B2
(45) Date of Patent: Sep. 9, 2025

(54) WIRE AND CATHETER ORGANIZER FOR ENDOVASCULAR PROCEDURE

(71) Applicant: Wisconsin Alumni Research Foundation, Madison, WI (US)

(72) Inventor: Dai Yamanouchi, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 138 days.

(21) Appl. No.: 17/547,804

(22) Filed: Dec. 10, 2021

(65) Prior Publication Data

US 2023/0181874 A1   Jun. 15, 2023

(51) Int. Cl.
*A61M 25/02* (2006.01)
*A61M 25/09* (2006.01)

(52) U.S. Cl.
CPC ............ *A61M 25/02* (2013.01); *A61M 25/09* (2013.01); *A61M 2025/0293* (2013.01)

(58) Field of Classification Search
CPC ............ A61M 39/08; A61M 2039/087; A61M 25/02; A61M 25/09; A61M 25/002; B65D 85/04; B65H 75/364
USPC ....................................... 242/159, 170, 570
See application file for complete search history.

(56) References Cited

U.S. PATENT DOCUMENTS

| | | | |
|---|---|---|---|
| 5,738,213 A | 4/1998 | Whiting et al. | |
| 6,902,057 B2 * | 6/2005 | Duffy ................. | A61M 25/002 206/364 |
| 9,889,462 B2 * | 2/2018 | Ahn .......................... | B05C 3/08 |
| 10,307,565 B2 * | 6/2019 | Sakaguchi ............. | A61B 50/00 |
| 2002/0157981 A1 * | 10/2002 | Whiting ............... | A61M 25/002 206/408 |
| 2006/0186256 A1 * | 8/2006 | Mogensen .......... | A61M 5/1418 242/405.1 |
| 2009/0277988 A1 * | 11/2009 | Hernik ............... | B65H 75/4481 242/478.2 |
| 2016/0206394 A1 * | 7/2016 | Lampropoulos ....... | B65D 81/22 |
| 2019/0276268 A1 * | 9/2019 | Akingba ............. | A61M 25/002 |
| 2021/0275775 A1 * | 9/2021 | Hong .................. | A61M 25/002 |

OTHER PUBLICATIONS

RingMaster Guide Wire Basin, "Merit Medical Systems, Inc".

* cited by examiner

*Primary Examiner* — Courtney B Fredrickson
*Assistant Examiner* — Kayla M. Turkowski
(74) *Attorney, Agent, or Firm* — Boyle Fredrickson, S.C.

(57) ABSTRACT

The present invention provides a guide wire and catheter disk holder that carries coiled guide wires and catheters with easy insertion of coiled guide wires and catheters through a side cutout on the holder allowing the user's hand to extend through the disk. The coiled guide wires and catheters are inserted substantially along a plane of the disk thus encouraging uncoiling and expanding of the wires and catheters into a longitudinal channel of the disk. The secured wire can be pulled out of the disk by holding and pulling the entire coiled wire, or by simply pulling the end of the wire while the rest of the wire is still secured inside the holder. Optionally, a spool may be inserted into the disk holder in order to wind up uncoiled wire and catheter within the disk holder.

12 Claims, 4 Drawing Sheets

WIRE AND CATHETER ORGANIZER FOR ENDOVASCULAR PROCEDURE

BACKGROUND OF THE INVENTION

The present invention relates to a medical holder for guide wires and catheters used during medical procedures, e.g., endovascular and endoscopic procedures, to hold and retain coiled guide wires and catheters.

Endovascular, or minimally invasive procedure, is used to treat cardiovascular disease affecting the blood vessels and involves making small incisions near the groin, the wrist, or other part of the body to access the blood vessels. Common problems treated with endovascular procedure is broad and may include coronary artery disease, stroke, peripheral arterial disease, venous thromboembolism, aneurysms, trauma, etc. Endovascular procedure offers many advantages to open surgery including a shorter recovery period, less discomfort, local or regional anesthesia instead of general anesthesia, smaller incision, less stress on the heart, and fewer risk to the patient with other medical conditions.

During endovascular procedure a guide wire is inserted through a small incision in the body and pushed through the blood vessel. Then, a catheter, i.e., a long, flexible, narrow tube, is inserted over the guide wire into the blood vessel. The catheter is advanced over the wire to avoid scraping and damaging the blood vessel lumen. The catheter may carry balloons or stents, i.e., small mesh tubes, used to assist with removing blockages and/or open narrowed areas of the blood vessel improving healthy blood flow. The catheter may carry other features including infusion lumen, atherectomy device to debulk plaque, ablation device, etc. Fluid may be injected through the catheter, for example, a contrast agent to assist with visualization of the blockages. An introducer sheath is usually used to secure the access into the blood vessel.

Many different guide wires and catheters may be used during endovascular procedure and may be selected based on desired qualities of the wire and catheter. The operator will frequently interchange guide wires and catheters during the endovascular procedure. For example, the specific wire may be chosen for a desired diameter, stiffness, and hydrophilic or non-hydrophilic composition, and the specific catheter may be chosen for a desired diameter, shape, end hole versus side hole, selective versus nonselective, glide versus non-glide, and hydrophilic or non-hydrophilic composition.

The guide wires and catheters must be kept in a sterilized environment but with limited space in the procedure room, it is common for guide wires and catheters to be accidentally dropped or contaminated and therefore become unusable during the procedure.

Common endovascular and catheterization procedures and treatments using guide wires and catheters include balloon angioplasty or percutaneous transluminal coronary angioplasty (PTCA), angioplasty with stent placement, placement of drug-eluting stents (DES), renal artery angioplasty/stenting/ablation, carotid artery stenting, e.g., transfemoral carotid artery stenting and transcarotid artery revascularization, intravascular brachytherapy (IVBT), atherectomy, thrombolysis, valvuloplasty, patent foramen ovale (PFO) and atrial septal defect (ASD) closures, transseptal catheterization, transcatheter aortic valve replacement, endovascular embolectomy procedure, and the like.

Other medical procedures commonly using guide wires and catheters include endoscopy where an operator will use an endoscope to examine the interior of a hollow organ or cavity of the body. Guide wires are used to help achieve access to a lumen or cavity during endoscopy procedure while catheters may be inserted over the guide wires and through the endoscope.

SUMMARY OF THE INVENTION

The present inventors have recognized that wire and catheter organization and handling during endovascular procedure is important in providing an efficient and safe procedure. Current methods commonly involve looping the wires and catheters by hand and clipping the wires in the loop or placing a weighted wet towel on top of the looped wires and catheters to keep them in place. However, these methods are clumsy and inefficient methods of holding and retaining the looped wires and catheters during procedure and are prone to droppage and contamination.

The wire and catheter holder provides a disk that easily receives pre-coiled wires and catheters (e.g., coiled by hand) or may be used with a spool to assist with coiling unwound wires and catheters into a coiled state within the holder, and then stores the wires and catheters within the disk holder until the wires and catheters are conveniently retrieved from the disk holder by dispensing the wire and catheter during procedure.

A circular cutout within the disk provides intuitive visual guidance to the user, guiding the user's hand toward the cutout opening for pulling pre-coiled wires across the disk holder through the circular cutout to assist with retaining the pre-coiled wires and catheters in a channel of the disk holder. A raised center axle may be used to retain a spool for winding the wires and catheters into a coiled state within the disk holder and to retain the wires and catheters within the disk holder during unwinding once the spool is removed.

It is thus a feature of at least one embodiment of the present invention to allow for intuitive insertion and removal of the coiled wire and catheter from the disk holder by pulling the coiled wire and catheter through a circular cutout across the disk holder along a substantially horizontal plane of the disk holder.

It is also a feature of at least one embodiment of the present invention to allow the disk holder to receive a spool retaining an end of the wire or catheter at a desirable angle for winding the wire or catheter into the disk holder and unwinding the wire or catheter from the disk holder.

It is also a feature of at least one embodiment of the present invention to allow the coiled wire or catheter to be submerged in a medical fluid such as sterile isotonic saline, sterile water, or the like to flush or rinse the wire or catheter while stored within the disk holder before use.

In one embodiment of the present invention, a guidewire and catheter holder for retaining coiled guidewire and catheters comprises a disk extending along a horizontal plane and having an upper surface opposite a lower surface, wherein a vertical axis passes through a center of the disk perpendicular to the horizontal plane; a rim of the disk supporting an inwardly extending lip surrounding an interior opening of the holder and holding a longitudinal channel, the longitudinal channel opening toward the vertical axis configured to receive the coiled guidewire and catheters along the horizontal plane perpendicular to the vertical axis; and at least one cutout hole formed within the rim of the disk and extended into an interior of the disk toward the center axis to remove an interior portion of the disk.

It is thus a feature of at least one embodiment of the present invention to provide intuitive entry of the guide wire into and across the holding disk to minimize the wire from being inserted at an angle and accidentally springing out before being captured within the channel.

The cutout hole may provide an unobstructed straight line path from an exterior of the disk to the longitudinal channel of an interior of the disk along the horizontal plane.

It is thus a feature of at least one embodiment of the present invention to easily guide the coiled wire along a straight line path through the cutout hole to expand into the retention channel when released.

The at least one cutout hole may be a circular segment.

It is thus a feature of at least one embodiment of the present invention to correlate the shape of the cutout hole with the shape of the user's first for intuitive entry of the first into the cutout hole.

A central angle subtending an arc of each cutout hole at an outer perimeter of the disk may be at least 30 degrees. Each cutout hole at the perimeter of the disk may have a width that is approximately a width of a first of an average human adult.

It is thus a feature of at least one embodiment of the present invention to allow the user's first to draw the wire toward and as close to the channel prior to releasing the wire to prevent the wire from accidentally springing out before being captured within the channel.

The outer edges of each cutout hole at the outer perimeter of the disk may provide inwardly extending overhangs defined by an upper wall of the inwardly extending lip extending inwardly into the cutout hole along the outer perimeter and above the cutout hole. Each of the overhangs may have a length this is at least 1 cm.

It is thus a feature of at least one embodiment of the present invention to capture the wire within the holder as the user's hand moves through the cutout hole so as to prevent the ungripped end of the looped wire from lifting up away from the cutout hole.

The inwardly extending lip may include a side wall extending upwardly from an upper surface of the disk and an upper wall extending inwardly toward the vertical axis from a top end of the upwardly extending wall to form outer walls of the channel.

It is thus a feature of at least one embodiment of the present invention to allow the coiled wire to naturally uncoil and expand outwardly along the horizontal plane to be captured by the channel when released and without additional human intervention.

The side wall may be curved outwardly and the upper wall may be curved upwardly to form a circular cross section. A gap may be formed between the upper wall and the disk to form a longitudinal slot along the inwardly extending lip and defining an opening of the longitudinal channel receiving the coiled guidewire and catheters.

It is thus a feature of at least one embodiment of the present invention to retain the coiled wire without an upper lid or cover which when removed would be prone to allowing the wires to spring out. The wire and catheter retainer is formed within the outer rim of the disk without the need for an upper lid or cover.

An upwardly extending axle may extend upwardly from at least one of the upper surface of the disk and lower surface of the disk along the vertical axis. The upwardly extending axle may include a center bore extending along the vertical axis. The axle may be a cylinder with a height extending along the vertical axis.

It is thus a feature of at least one embodiment of the present invention to prevent the wires from being pulled out from the disk when the wires are being dispensed and unwound from the disk. The axle acts as a "spool" to retain the loops of the wire as the wire is being pulled at one end of the wire.

The disk may be a circle that has a diameter that is greater than 10 cm and less than 50 cm or greater than 15 cm and less than 50 cm.

It is thus a feature of at least one embodiment of the present invention to allow the disk to support winding of long lengths of wire and catheter needed during surgery.

A spool may provide a cylinder sized to be inserted into the disk and rotated with respect to the disk wherein the spool is configured to retain an end of the wire or catheter for winding.

It is thus a feature of at least one embodiment of the present invention to permit the holder to be used with a spool that can assist with winding the wire inside the holder.

The spool may be configured to retain an end of the wire or catheter within a pair of substantially perpendicularly extending slits of the spool.

It is thus a feature of at least one embodiment of the present invention to secure the end of the wire or catheter without pinching the wire or catheter which may cause damage to the wire of catheter.

The spool may be configured to retain an end of the wire or catheter at an angle wherein the wire or catheter is configured to extend from the spool at an angle that is not tangent to an outer perimeter of the spool.

It is thus a feature of at least one embodiment of the present invention wind and unwind the wire and catheter at a desirable angle consistent with the insertion angle needed by the physician during surgery.

The disk may support at least one drainage hole permitting fluid to flow between the upper surface of the disk and the lower surface of the disk.

It is thus a feature of at least one embodiment of the present invention to allow the wire and catheter to be flushed or rinsed with medical fluid prior to use.

The holder may be sold as part of a kit further including at least one of a disk organizer box, wire diverter, and guard rail.

An alternative embodiment of the present invention provides a method of retaining coiled guidewire and catheters, the method comprising the steps of: providing a guidewire and catheter holder having a disk extending along a horizontal plane and having an upper surface opposite a lower surface, wherein a vertical axis passes through a center of the disk perpendicular to the horizontal plane; a rim of the disk supporting an inwardly extending lip holding a longitudinal channel, the longitudinal channel opening toward the vertical axis; and at least one cutout hole formed within the rim of the disk and extended into an interior of the disk toward the center axis to remove an interior portion of the disk; pulling coiled guidewire and catheter through the cutout hole of the disk and into the disk along the horizontal plane perpendicular to the vertical axis; and releasing the coiled guidewire and catheter so that the longitudinal channel receives the coiled guidewire and catheter along the horizontal plane perpendicular to the vertical axis.

The coiled guidewire and catheter may be pulled under inwardly extending overhangs defined by an upper wall of the inwardly extending lip extending inwardly into the cutout hole along the outer perimeter and above the cutout hole.

These particular objects and advantages may apply to only some embodiments falling within the claims and thus do not define the scope of the invention.

DETAILED DESCRIPTION OF THE INVENTION

Figure 1:
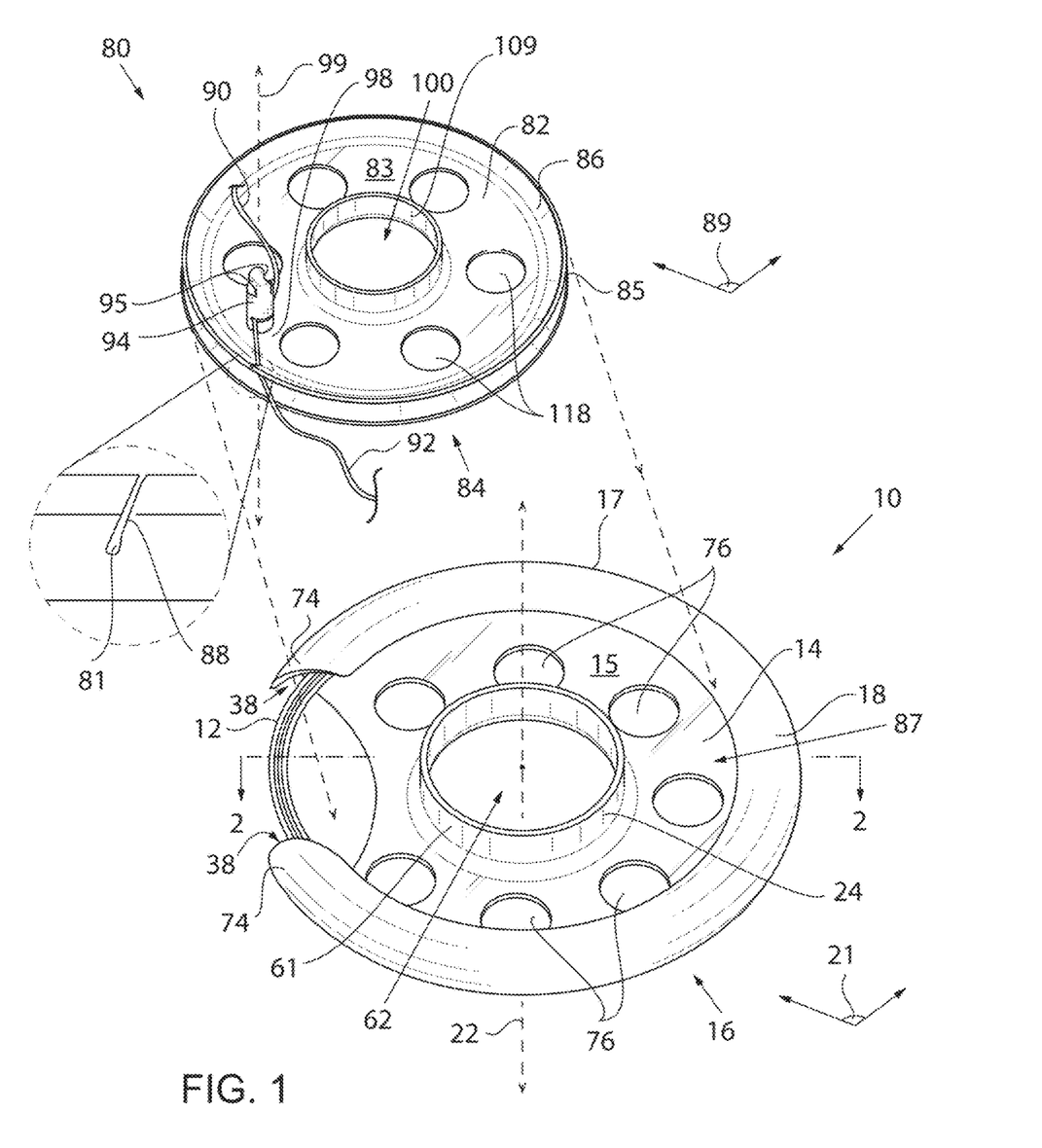
FIG. 1 is a perspective view of a guide wire and catheter disk holder of the present invention shown carrying a cutout guiding intuitive entry of pre-coiled guidewire and catheter into the disk holder and around a cylinder-shaped center axle with a center bore, and optionally, receiving a spool facilitating the winding of wire and catheter into the disk holder, the spool retaining an end of the wire and catheter at an angle within substantially perpendicularly extending slits of the spool.

Referring to FIG. 1, a disk holder 10 for retaining coiled wires and catheters 12 may take the form of a circular disk 14 having a planar upper surface 15 opposite a planar lower surface 16. An outer rim 17 forms an outer perimeter of the disk 14, the outer rim 17 providing an inwardly extending lip 18 forming a channel 38 capable of retaining coiled wires and catheters 12 therein. A center vertical axis 22 of the disk 14 may extend vertically through a center of the disk 14 and is substantially perpendicular to a plane 21 of the disk 14. An upwardly extending axle 24 may extend along the center vertical axis 22 and may optionally support a spool 26 thereon, as described in further detail below.

The disk 14 may be sized to retain long lengths of coiled wire and catheter 12. The disk 14 may have an outer diameter that is at least 10 cm and at least 15 cm and at least 20 cm at least 30 cm and at least 40 cm and approximately 10 cm to 50 cm and approximately 15 cm to 50 cm and approximately 18 cm and providing a desirable outer circumference that is able to retain coiled wires and catheters 12 which may be as long as 180 cm to 450 cm in length (from a tip to a tail of the wire and catheter). The disk 14 may have a thickness (measured along the center vertical axis 22) that is approximately 1 cm to 5 cm.

The disk 14 may be constructed of a thermoplastic material which may be formed using a known plastic molding process, for example, injection molding process, extrusion molding process, compression molding, blow molding, rotation molding, thermoforming, and the like. The disk 14 may alternatively be formed using known 3D printing processes. Thermoplastic materials that may be used to construct the disk 14 include polycarbonate, polypropylene, polyethylene, or the formulation of custom polymers. The thermoplastic materials are desirably medical grade, high wear, temperature resistant and corrosion resistant.

Figure 2:
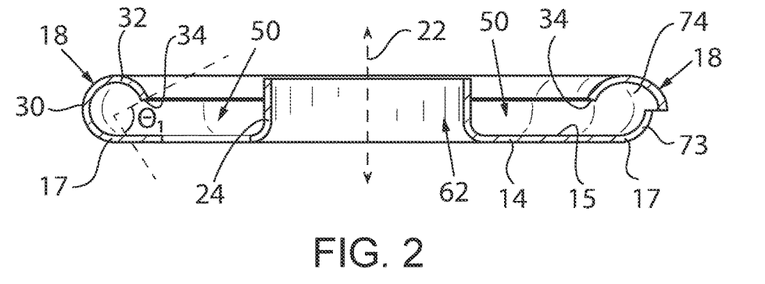
FIG. 2 is a cross-section of the disk holder taken along line 2-2 of FIG. 1 and showing the circular cross section of the channel formed at a rim of the disk holder and overhanging lips at outer edges of the cutout.

Referring also to FIG. 2, the outer rim 17 of the disk 14 supports the inwardly extending lip 18 extending, first, upwardly from the upper surface 15 of the disk 14 and, second, inwardly toward the center vertical axis 22. The inwardly extending lip 18 is formed of a vertically extending wall 30 extending upwardly from the outer rim 17 of the disk 14 and then extending to a horizontally extending wall 32 extending inwardly toward the center vertical axis 22 from an upper end of the vertically extending wall 30.

The vertically extending wall 30 may be a curved wall that curves outwardly away from the center vertical axis 22 and the horizontally extending wall 32 may be a curved wall that curves upwardly away from the upper surface 15 of the disk 14. In this respect, the vertically extending wall 30 and the horizontally extending wall 32 form a continuously curved wall forming a substantially circular cross section with the bottom disk 14. The vertically extending wall 30, horizontally extending wall 32, and the disk 14 form the circular channel 38 extending longitudinally around the outer perimeter of the disk 14.

An inner edge 34 of the horizontally extending wall 32 may curve downwardly toward the upper surface 15 of the disk 14 leaving a gap forming a longitudinal slot opening 50 between the inner edge 34 of the horizontally extending wall 32 and the upper surface 15 of the disk 14. The longitudinal slot opening 50 extends longitudinally along the circular channel 38 and along the outer rim 17 of the disk 14.

The longitudinal slot opening 50 between the inner edge 34 of the horizontally extending wall 32 and the upper surface 15 of the disk 14 permit the coiled wires and catheters 12 to enter the circular channel 38 formed by the vertically extending wall 30, the horizontally extending wall 32, and the disk 14 along an outward radial direction from and perpendicular to the center vertical axis 22. The longitudinal slot opening 50 is wide enough (a width of the longitudinal slot opening 50 measured along the center vertical axis 22) to allow the coiled wires and catheters 12 to enter the circular channel 38 but is narrow enough to prevent the coiled wires and catheters 12 from accidentally springing out from the circular channel 38.

The vertically extending wall 30, horizontally extending wall 32, and the disk 14 have a substantially circular cross section where the longitudinal slot opening 50 may be defined by a minor sector of the circular cross section of the circular channel 38 and has a central angle ($\theta_1$) that is, for example, at least 40 degrees and at least 50 degrees and at least 60 degrees and at least 70 degrees and at least 80 degrees and at least 90 degrees and/or is less than 110 degrees and less than 100 degrees and less than 90 degrees and less than 80 degrees and less than 70 degrees and less than 60 degrees. The central angle ($\theta_1$) of the minor sector formed by the longitudinal slot opening 50 may be, for example, between 40 to 110 degrees and between 50 to 100 degrees and between 60 to 90 degrees and between 70 to 80 degrees.

The disk 14 may support the upwardly extending axle 24 extending upwardly from the upper surface 15 of the disk 14 along the center vertical axis 22 to provide an upwardly extending shaft or rod on which the spool 26 may rotate. In the embodiment shown in FIGS. 1 and 2, the axle 24 is a hollow cylinder or tube providing an outer cylindrical wall 61 surrounding a central bore 62 passing through the center vertical axis 22. In some embodiments, an upper end of the axle 24 may flare outwardly or may have an outwardly extending upper edge. The axle 24 may have an outer diameter of approximately 10 cm to 30 cm.

Figure 3:
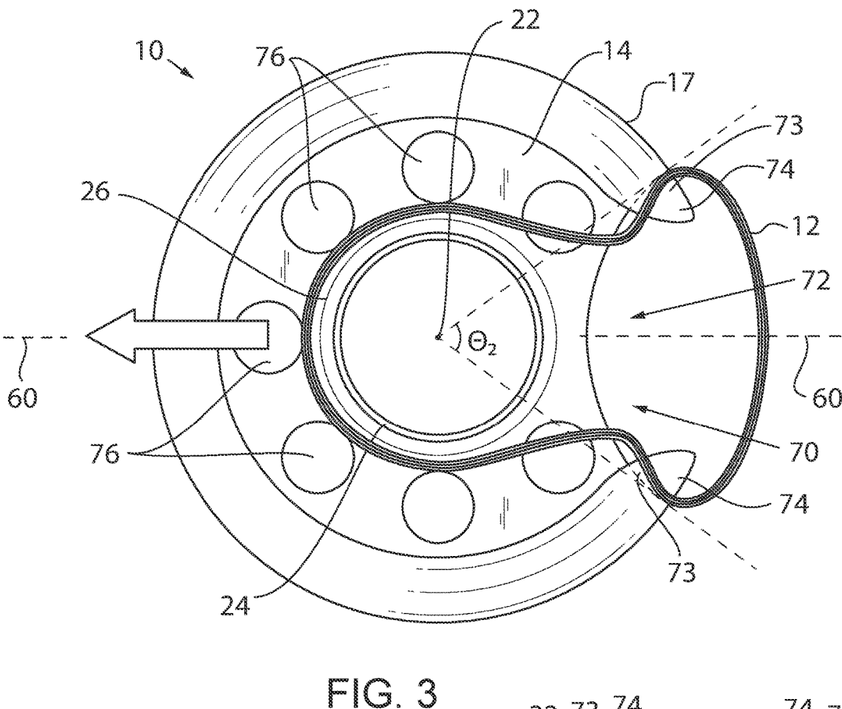
FIG. 3 is a top plan view of the disk holder of FIG. 1 showing a direction of entry of the pre-coiled guidewire and catheter through the cutout within the rim and toward and around the center axle.

Referring now to FIGS. 1 and 3, the disk 14 may include a circular cutout 70 formed within the disk 14 permitting improved entry and insertion of the coiled wires and catheters 12 into the disk 14. The circular cutout 70 may be a partial circle or circular segment shaped opening extending through the outer rim 17 of the disk 14 at an insertion end 72 of the disk 14.

The circular cutout 70 may have an arc length extending along the outer perimeter of the disk 14 where a central angle ($\theta_2$) subtended by an arc of the circular cutout 70 along the perimeter of the disk 14 is at least 40 degrees and at least 50 degrees and at least 60 degrees and at least 70 degrees and at least 80 degrees and at least 90 degrees and/or is less than 110 degrees and less than 100 degrees and less than 90 degrees and less than 80 degrees and less than 70 degrees and less than 60 degrees. The central angle ($\theta_2$) subtending the arc of the circular cutout 70 at the perimeter of the disk 14 may be between 40 to 110 degrees and between 50 to 100 degrees and between 60 to 90 degrees and between 70 to 80 degrees.

The circular cutout 70 may have a length extending from the outer rim 17 of the disk 14 into an interior of the disk 14 toward the center vertical axis 22. The circular cutout 70 may extend at least 10% and at least 20% and at least 30% and at least 40% and at least 50% and at least 60% of a length of an outer diameter of the disk 14. In this respect, the circular cutout 70 may extend toward the center of the disk 14.

Figure 4:
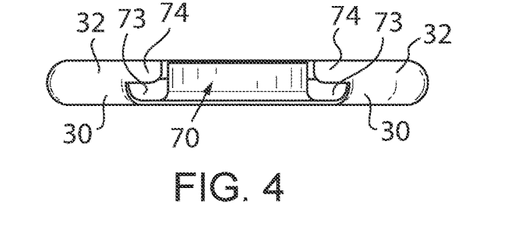
FIG. 4 is a front elevation view of the disk holder of FIG. 1 showing the overhanging lips at the outer edges of the cutout.

Referring now to FIGS. 2, 3 and 4, the outer edges 73 of the circular cutout 70 may provide overhanging rims 74 which assist with retaining the coiled wires and catheters 12 as they are being inserted into the disk 14. The overhanging rims 74 are formed by a protruding edge of the horizontally extending wall 32 extending above and into the circular cutout 70, thus trapping the coiled wires and catheters 12 between the overhanging rims 74 and the disk 14 at the outer edges of the circular cutout 70 as the coiled wires and catheters 12 are being drawn into the disk 14. Each of the overhanging rims 74 may extend horizontally over and into the circular cutout 70 at the outer perimeter of the disk 14 a distance of at least 1 cm and at least 2 cm and at least 3 cm and at least 4 cm and at least 5 cm.

Referring now to FIGS. 1, 3 and 4, a width of the circular cutout 70 (measured across the cutout 70 along the plane 21 of the disk 14) may be approximately a width of an average human adult hand when formed into a fist, thus allowing the user's hand to draw the coiled wires and catheters 12 into and through the disk 14 as best seen in FIG. 3. In one embodiment, the width of the circular cutout 70 measured across the circular cutout 70 may be at least 7 cm and at least 7.5 cm and at least 8 cm and at least 8.5 cm and approximately 8 cm to 9 cm. The circular cutout 70 also provides a visual indication to the user to direct their hand to insert the coiled wires and catheters 12 into the disk 14 at the position of the circular cutout 70.

Additional circular holes 76 may be formed within the disk 14 and may be evenly spaced around the axle 24. For example, the disk 14 may include seven circular holes 76 extending evenly around the axle 24. The circular holes 76 provide additional finger grips permitting a user to grip the disk 14 by placing the user's fingers through the holes 76. The circular holes 76 also permit fluids to drain through the disk 14 when the disk is submerged in medical fluids, for example, sterile water or saline for cleaning the coiled wires and catheters 12 stored within the disk 14. Each of the circular holes 76 may have a diameter of approximately 5 cm to 15 cm.

Referring to FIG. 3, in use, the wires and catheters 12 are coiled by hand into concentric circles or rings having a diameter sized to be smaller than an outer diameter of the disk 14 so that they can inserted therein. The loops of coiled wires and catheters 12 are held by the user's hand at one end of the loops and inserted into the disk 14 through the circular cutout 70 by drawing the coiled wires and catheters 12, with the held end of the loops inserted first through the circular cutout 70 along a substantially horizontal path 60 parallel to the plane 21 of the disk 14 at the insertion end 72 so that the coiled wires and catheters 12 are trapped under the overhanging rims 74 as they are being inserted.

The coiled wires and catheters 12 are pulled though the disk 14 to an opposite end of the insertion end 72 and pulled around the axle 24 in the process. Once the entire loop of coiled wires and catheters 12 is pulled through the circular cutout 70, the user may release their grasp on the coiled wires and catheters 12 allowing the loop of coiled wires and catheters 12 to uncoil and expand outwardly, radially along the plane 21 to naturally enter the circular channel 38.

When the user desires to dispense the coiled wires and catheters 12 from the disk 14, the user may rotate the coiled wires and catheters 12 within the disk 14 until an end of the coiled wires and catheters 12 is located through the circular cutout 70. The end of the coiled wires and catheters 12 is then subsequently pulled outwardly through the circular cutout 70 to unwind the coiled wires and catheters 12 progressively until the entire loop of coiled wires and catheters 12 are pulled out of the disk 14 through the circular cutout 70. The axle 24 supports unwinding of the coiled wires and catheters 12 by retaining the looped configuration of the coiled wires and catheters 12 and preventing the coiled wires and catheters 12 from springing out of the disk 14 during unwinding. The axle 24 thus acts like a "spool" during unwinding of the coiled wires and catheters 12 from the disk 14.

Referring again to FIG. 1, in some embodiments, the disk 14 may support the insertion of a spool 80 therein which facilitates the winding of the coiled wires and catheters 12 within the disk 14 itself rather than being pre-wound outside of the disk 14 as described above. This may be preferred, for example, if the user is unable to or is less efficient at coiling the wires and catheters 12 by hand.

The spool 80 may be formed of a smaller spool disk 82 having a flat upper surface 83 opposite a flat lower surface 84. The spool disk 82 has an outer diameter that is smaller than a diameter of a spool insertion opening 87 defined by the inner edge 34 of the inwardly extending lip 18 of the disk 14 so that the spool 80 can be inserted inside the inwardly extending lip 18 of the disk 14.

An outer perimeter of the spool disk 82 is defined by a rim 85 of the spool 80 providing by an upwardly extending wall 86. The upwardly extending wall 86 may extend upwardly from the upper surface 83 of the spool disk 82 around a perimeter of the spool disk 82 and may be a curved wall that curves inwardly and then outwardly to provide a narrower center and wider top and bottom of the upwardly extending wall 86. The upwardly extending wall 86 may generally form a cylinder or hourglass shape on which the coiled wires and catheters 12 may be wound. The upwardly extending wall 86 may have a height of approximately 1 cm to 4 cm.

The upwardly extending wall 86 may contain a vertical slit 88 cut into a top edge of the upwardly extending wall 86 and extending along a plane that is substantially vertical or at an angle close to vertical for receiving and retaining the unwound wire and catheter 92 therein. The angle of the vertical slit 88 may be at an approximately 60 to 90 degree angle with respect to a plane 89 of the spool disk 82. The vertical slit 88 may have a width that is less than 0.5 cm and less than 0.4 cm and less than 0.3 cm and may be wide enough to prevent the unwound wire and catheter 92 from being pinched within the slit. The vertical slit 99 may have a length that is approximately 0.5 cm to 2 cm and may extend approximately half a height of the upwardly extending wall 86. The vertical slit 88 may include a circular notch 81 at the bottom end to assist with catching and retaining the inserted unwound wire and catheter 92 within a bottom of the slit 88.

The upper surface 83 of the spool 80 also supports a crank knob 94 formed by a cylindrical rod extending upwardly from the upper surface 83 of the spool disk 82 in close proximity to the vertical slit 88. The crank knob 94 may contain a horizontal slit 98 cut into a side of the crank knob 94 and extending along a plane that is substantially horizontal or at an angle close to horizontal for receiving and retaining an end 90 of the unwound wire and catheter 92. The angle of the horizontal slit 98 may be at an approximately 0 to 30 degree angle with respect to the plane 89 of the spool disk 82. The horizontal slit 98 may have a width that is less than 0.5 cm and less than 0.4 cm and less than 0.3 cm and may be wide enough to prevent the unwound wire and catheter 92 from being pinched within the slit. The horizontal slit 98 may have a length that is approximately 0.5 cm to 2 cm and may extend approximately halfway across the crank knob 94. A top end of the crank knob 94 may include opposed depressions 95 for receiving the user's fingers for gripping the crank knob 94.

The vertical slit 88 and the horizontal slit 98 of the upwardly extending wall 86 and the crank knob 94, respectively, are aligned such that the unwound wire and catheter 92 may be inserted into both slits 88, 98 at the same time along a straight line 99. The angle of the straight line 99 is along a secant line that intersects the perimeter of the spool 80 at two distinct points but does not pass through a center of the spool disk 82. The unwound wire and catheter 92 may extend outwardly from the spool 80 at an approximately 50 to 70 degree angle with respect to a tangent line at the vertical slit 88 on the perimeter of the spool 80.

The vertical slit 88 and the horizontal slit 98 extend along substantially perpendicular planes to retain the end 90 of the unwound wire and catheter 92 and to hold the end 90 of the unwound wire and catheter 92 securely in place without pinching the wire and catheter 92. It is understood that the vertical slit 88 and the horizontal slit 98 may extend along planes close to perpendicular, but not perpendicular, so that the planes intersect at an angle between the planes that is, for example, between 60 to 90 and between 70 to 90 degrees and between 80 to 90 degrees, but still securing the end 90 of the unwound wire and catheter 92.

A spool axle 109 formed by a cylinder extending upwardly from the upper surface 83 of the spool disk 82 at the center of the spool disk 82 may support a center spool bore 100. The center spool bore 100 of the spool disk 82 has an outer diameter that is larger than the outer diameter of the axle 24 of the disk 14 to permit the center spool bore 100 to receive the axle 24 of the disk 14 therein along the center vertical axis 22. The spool bore 100 of the spool 80 when received onto the axle 24 of the disk 14 permits rotation of the spool 80 with respect to a stationary disk 14 by rotating the spool 80 inside the disk 14.

Additional circular holes 118 may be formed within the spool disk 82 and may be evenly distributed around the cylindrical spool axle 109. Similar to the circular holes 76 of the disk 14, the circular holes 118 provide additional finger grips permitting a user to grip the spool 80 by placing the user's fingers through the holes 118. Each of the circular cutout holes 110 may have a diameter of approximately 5 cm to 15 cm.

In use, the unwound wire and catheter 92 is inserted into the horizontal slit 98 of the crank knob 94 so that the end 90 extends outwardly from the crank knob 94. The opposite end is inserted into the vertical slit 88 of the upwardly extending wall 86, with the extended length of unwound wire and catheter 92 extending outwardly from the spool 80 at the vertical slit 88 of the upwardly extending wall 86 along the straight line 99.

Next, the spool 80 is inserted into the insertion opening 87 of the disk 14 within the inwardly extending lip 18, and the spool bore 100 extends around the axle 24 of the disk 14 so that the spool 80 can rotate thereon. To wind the unwound wire and catheter 92 into the disk 14, the user rotates the spool 80 in a circular motion with the user's fingers grasping the opposed depressions 95 of the crank knob 94 and rotating the crank knob 94 clockwise or counterclockwise generally along the direction of the straight line 99 to allow the unwound wire and catheter 92 to wind around the spool 26.

Once the wire and catheter 92 is wound within the disk 14, the user may remove the end 90 of the coiled wire and catheter 12 from the spool 80 (i.e., from both slits 88, 98) causing the coiled wire and catheter 12 to uncoil and expand outwardly, radially along the plane 21 to naturally enter the circular channel 38. The user may then remove the spool 80 from the disk 14. The coiled wire and catheter 12 is retained within the disk 14 within the circular channel 38 in a similar manner as the pre-coiled wire and catheter described above.

When the user desires to dispense the coiled wires and catheters 12 from the disk 14, the user may rotate the coiled wires and catheters 12 within the disk 14 until an end of the coiled wires and catheters 12 is found through the circular cutout 70 and then subsequently unwound and pulled out of the disk 14 through the circular cutout 70.

Figure 5:
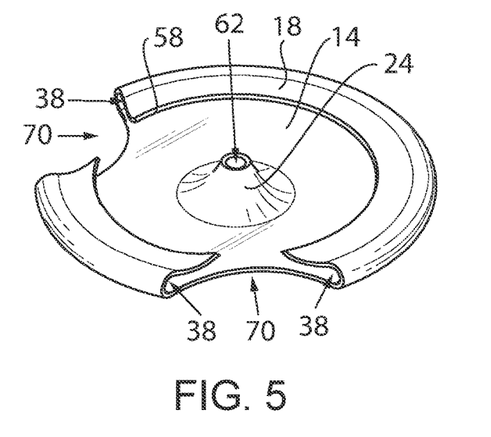
FIG. 5 is a perspective view of an alternative embodiment of the present invention providing a disk holder with a pair of cutouts at an end of the disk holder permitting intuitive entry of the pre-coiled guidewire and catheter into the disk holder at two locations and providing a cone-shaped center axle with a center bore.

Referring now to FIG. 5, alternative embodiments of the present invention may include variations of the inwardly extending lip 18 of the disk 14 but which still permit entry and retention of the coiled wires and catheters 12 within the circular channel 38. For example, an alternative embodiment of the present invention may further include an inner edge 58 of the horizontally extending wall 32 that flares upwardly along the center vertical axis 22 as seen in FIG. 5.

Figure 6:
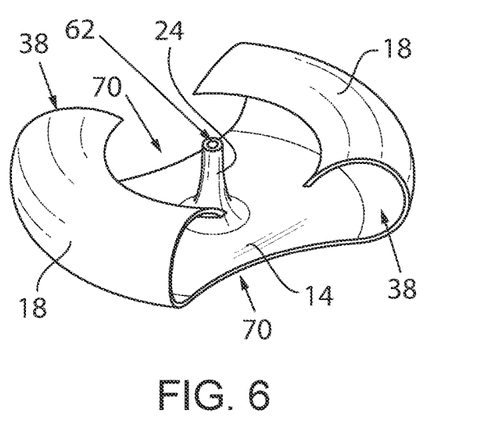
FIG. 6 is a perspective view of an alternative embodiment of the present invention providing a disk holder with a pair of opposed side cutouts permitting intuitive entry of the pre-coiled guidewire and catheter into the disk holder at two locations and providing a trumpet-shaped center axle with a center bore.
Figure 8:
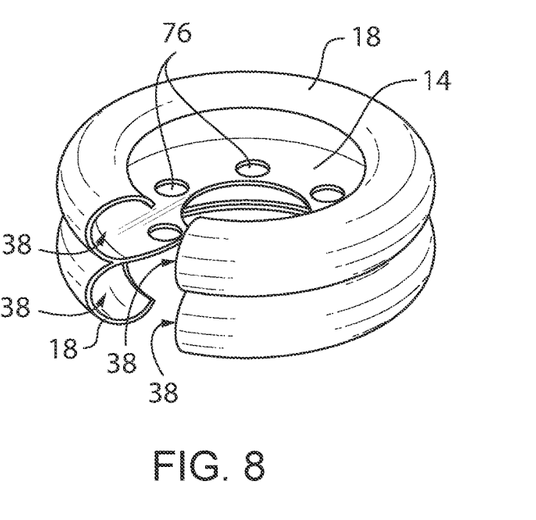
FIG. 8 is a perspective view of an alternative embodiment of the present invention providing a disk holder with a cutout extending through a center of the disk thus eliminating the center axle and supporting a channel on an opposite side of the disk to support more than one loops of pre-coiled guidewire and catheter.

Referring now to FIGS. 5, 6 and 8, alternative embodiments of the present invention may also include variations of the circular cutout 70 of the disk 14 which still permit intuitive entry of the coiled wires and catheters 12 into the disk 14 and extending around the axle 24.

Referring specifically to FIG. 5, an alternative embodiment of the present invention may include one or more circular cutouts 70 extending around the disk 14. For example, the disk 14 may include a pair of circular cutouts 70 spaced apart at one end of the disk 14 permitting entry of the coiled wires and catheters 12 into the disk 14 at two entry points. The pair of circular cutouts 70 may permit entry of the coiled wires and catheters 12 into the disk 14 at two entry points.

Referring specifically to FIG. 6, an alternative embodiment of the present invention may include a disk 14 with a pair of circular cutouts 70 spaced apart at opposite ends of the disk 14 permitting entry of the coiled wires and catheters 12 into the disk 14 at two opposed entry points. The pair of circular cutouts 70 may permit entry of the coiled wires and catheters 12 into the disk 14 at two entry points but on opposite ends of the disk 14.

Referring specifically to FIG. 8, an alternative embodiment of the present invention may include a disk 14 with a single circular cutout 70 which extends deeper into the interior of the disk 14 and therefore removes a center area of the disk 14 receiving the center vertical axis 22. In this respect, the disk 14 may omit the axle 24 from the disk 14. When the axle 24 is removed from the disk 14, the user may dispense the coiled wires and catheters 12 from the disk 14 by pulling the entire loop of coiled wires and catheters 12 out from the disk 14 without unwinding the coiled wires and catheters 12 from the disk 14 by pulling on the end 90 of the coiled wires and catheters 12.

It is understood that the disk 14 may carry any number of circular cutouts 70, for example, one, two, three, four or more circular cutouts 70 extending around the axle 24 at spaced apart positions and at any location around a perimeter of the disk 14.

Figure 7:
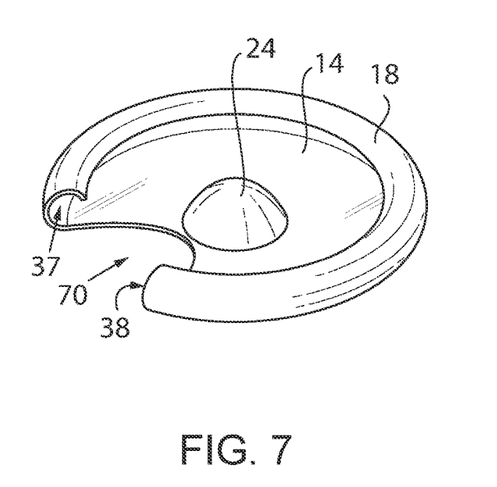
FIG. 7 is a perspective view of an alternative embodiment of the present invention providing a disk holder with a single cutout permitting intuitive entry of the pre-coiled guidewire and catheter into the disk holder and providing a paraboloid shaped center axle without a center bore.

Referring now to FIGS. 5, 6, and 7, alternative embodiments of the present invention may also provide variations to a shape of the axle 24 and may or may not include the central bore 62 and which allow the spool 26 to rotate thereon.

Referring specifically to FIG. 5, in an alternative embodiment, the axle 24 may be a cone shape with a circular base of the cone formed on the upper surface 15 of the disk 14 and extending upward to a tip or vertex of the cone along the center vertical axis 22, the cone having a central bore 62 passing through the center vertical axis 22. The cone shaped axle 24 may support thereon the spool 80.

Referring specifically to FIG. 6, in an alternative embodiment, the axle 24 may a trumpet shape, generally similar to the cone shaped axle of FIG. 5 but with an elongated tip. A circular base of the cone is formed on the upper surface 15 of the disk 14 and extends upwardly to a thin and narrow tip of the trumpet along the center vertical axis 22, the trumpet having a central bore 62 passing through the center vertical axis 22. The cone shaped axle 24 may support thereon the spool 80.

Referring specifically to FIG. 7, in an alternative embodiment, the axle 24 may be paraboloid shape with a circular base of the paraboloid formed on the upper surface 36 of the disk 14 and extending upward to a rounded tip or vertex of the paraboloid along the center vertical axis 22, the paraboloid supporting a spool 80 thereon but omitting the central bore 62.

It is understood that the axle 24 may take various three dimensional shapes, including but not limited to cylinders, cones, paraboloids, cubes, cuboids, spheres, prisms, pyramids, and the like, providing an upwardly extending shaft or rod that may support the spool 80 thereon. The axle 24 may include a central bore 62 or may omit the central bore 62.

Referring now to FIG. 8, an alternative embodiment of the present invention may include a disk 14 that supports more than one inwardly extending lip 18 and more than one circular channel 38. The disk 14 may support the inwardly extending lip 18 at the upper surface 15, as described above with respect to FIGS. 1 through 7, but an additional inwardly extending lip 18 and circular channel 38 may be positioned on the opposed, lower surface of the disk 14, in addition to the upper surface 15 of the disk 14, to provide more than one channel 38. In this respect, more than one loops of coiled wires and catheters 12 may be held and retained within the more than one channel 38 of a single disk 14. The disk 14 may optionally include an axle 24 on each side of the disk 14 to support the positioning of the spool 26 therein or may omit the axle 24 as shown.

Figure 9:
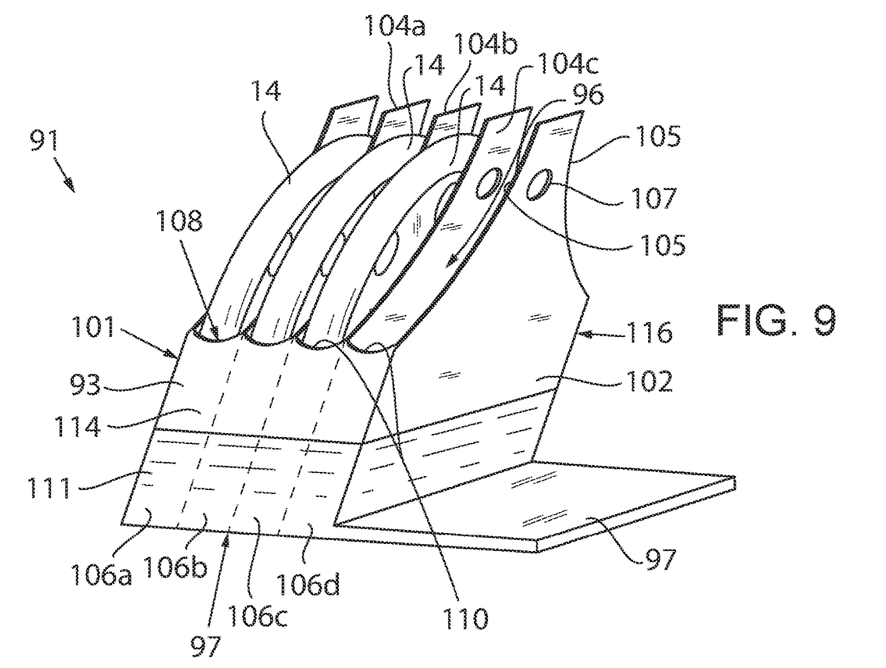
FIG. 9 is a disk container used in connection with one or more disk holders as shown in FIGS. 1 through 8 and which may be sold with the disk holders in a kit and has separate vertical compartments receiving the disk holders permitting the disk holders to be partially submerged in a medical fluid and facilitating uncoiling of the wire and catheter from the disk holders.

Referring now to FIG. 9, the present invention may further include a disk organizer 91 that may hold one or more disks 14 therein in a stacked configuration. The disk organizer 91 may be a rectangular box 93 having an open top 96 opposite a bottom wall 97, a front wall 114 opposite a rear wall 116 extending upwardly from a front and rear of the bottom wall 97, and left and right side walls 101, 102 positioned between the front wall 114 and the rear wall 116. The rectangular box 93 may be in the form of a vertical rectangular prism where the front wall 114, rear wall 116, and left and right side walls 101, 102 are slanted toward the right side wall 103.

The left and right side walls 101, 102 may extend higher than the front wall 114 and the rear wall 116. The front and rear wall 114, 116 may have a height that is approximately equal to approximately half a diameter of the disk holder 10. The height of the front and rear wall 114, 116 may be approximately 15 to 25 cm. The left and right side walls 101, 102 may have a height that is approximately equal to the diameter of the disk holder 10. The height of the left and right side walls 101, 102 may be approximately 30 to 50 cm. The bottom wall 97 may extend past the right side wall 102 to provide a longer base for improved stability.

The left and right side walls 101, 102 may contain upper left and right side cutouts 105 and a central hole opening 107 assisting with insertion and removal of the disk holder 10 from the rectangular box 93.

Separator plates 104a, 104b, 104c may be positioned inside the rectangular box 93 in slanted configuration and extend in parallel with the slanted left and right side walls 101, 102 to separate an inner volume of the rectangular box 93 into separate compartments 106a, 106b, 106c, 106d. The distance between adjacent separator plates 104a, 104b, 104c, between the left side wall 101 and the separator plate 104a, and between the separator plate 104c and the right side wall 102 is greater than a width of the disk holder 10 (a width of the disk holder measured along the center vertical axis 22) so that the disk holder 10 is sized to fit between adjacent separator plates 104a, 104b, 104c, between the left side wall 101 and the separator plate 104a, and between the separator plate 104c and the right side wall 102. The separator plates 104a, 104b, 104c may extend higher than the front wall 114 and the rear wall 116 and may be about the same height as the left and right side walls 101, 102.

The front wall 114 and rear wall 116 may have a scalloped upper edge 108 where a semi-circular cutout 110 of the scalloped upper edge 108 is formed at the front and rear edges of each slanted compartment 106a, 106b, 106c, 106d. Therefore, coiled wire and catheter 12 extending outward from the disk 14 may rest upon the smooth edge of the semi-circular cutout 110 during uncoiling and dispensing of the coiled wire and catheter 12 from the disk and from the rectangular box 93.

The separator plates 104 may still permit fluid flow between the separate compartments 106a, 106b, 106c, 106d, for example, by leaving a gap between the separator plates 104a, 104b, 104c and the bottom wall 97 or by hole openings formed within the separator plates 104a, 104b, 104c. In this manner, the rectangular box 93 may be filled with medical fluids such as sterile isotonic saline, sterile water, or the like which may be permitted to flow between the separate compartments 106a, 106b, 106c 106d.

In use, one or more disk holders 10 may be inserted into the separate compartments 106a, 106b, 106c 106d so that the plane 21 of the disk holders 10 extend along the separator plates 104a, 104b, 104c and can be neatly organized in the surgical environment.

The rectangular box 93 may be filled with a medical fluid before or after the insertion of the disk holders 10 into the rectangular box 93. The bottom end of the disk holders 10 may be submerged in the medical fluid 111 in order to flush or rinse the coiled wire and catheter 12. The disk holders 10 may be rotated within the rectangular box 93 in order to rinse the entire length of the coiled wire and catheter 12.

When it is desired to dispense the coiled wire and catheter 12 from the disk holders 10, the disk holders 10 may be rotated within the rectangular box 93 in order to locate the end 90 of the coiled wire and catheter 12 and the end 90 of the coiled unwound wire and catheter 92 may be pulled out along the semi-circular cutout 110 of the front wall 114 or rear wall 116.

Figures 10, 11:
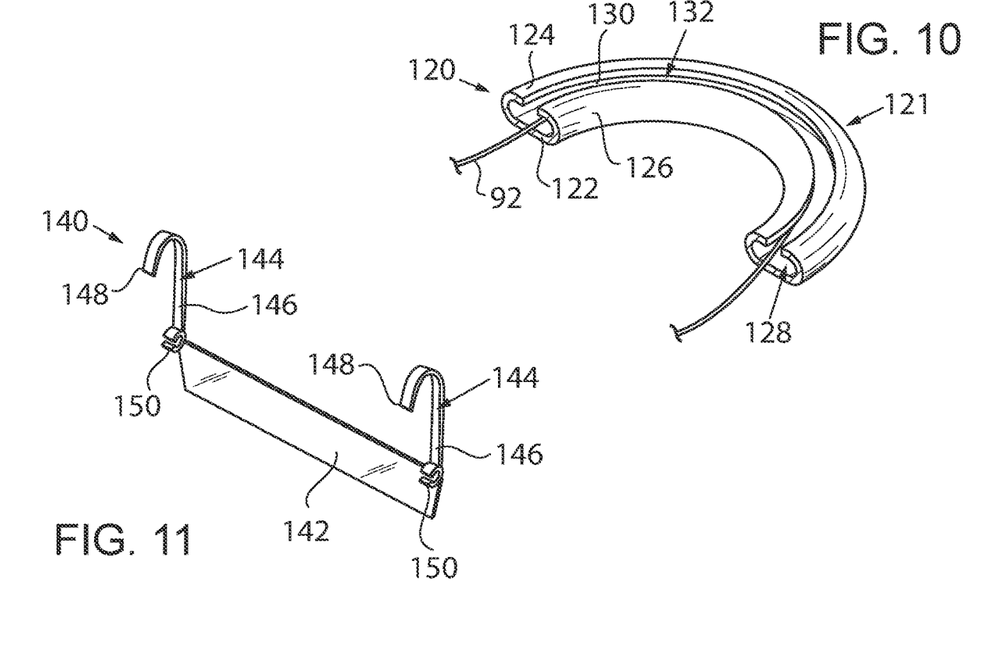
FIG. 10 is a wire and catheter diverter which may be sold with the disk holder in a kit and is formed by a U-shaped channel changing the direction of the wire and catheter by 180 degrees and may be used when the entry to the blood vessel is not at an appropriate direction to perform the procedure.
FIG. 11 is a wire holder which may be sold with the disk holders in a kit and is formed by a shield holding a set of hooks and wire retention clips with the shield placed at the edge of a sterile drape, the set of hooks preventing the wires and catheter from dropping off from the side of the sterile drape, and the wire retention clips securing wires and catheters on the table.

Referring now to FIG. 10, the present invention may further include a wire and catheter diverter 120 that may be used to change the direction of the unwound wire and catheter 92 during surgery, for example, to assist the physician in obtaining a desired angle of the unwound wire and catheter 92 for insertion into the body of the patient.

The wire and catheter diverter 120 may be comprised of a U-shaped rail 121 comprising an arched bottom wall 122, a left side wall 124 extending upwardly from a left edge of the arched bottom wall 122, and a right side wall 126 extending upwardly from a right edge of the arched bottom wall 122. The left side wall 124 and the right side wall 126 are curved walls that curve outwardly from the edges of the U-shaped bottom wall 112 and bend inwardly toward each other at a top end 130. In this respect, the left side wall 124 and right side wall 126 form a continuously curved wall forming a substantially oval cross section with the arched bottom wall 122 to form am oval channel 128.

The left side wall 124 and right side wall 126 extend toward each other but leave a gap to form a slot opening 132 between the inner edges of the left side wall 124 and right side wall 126 at the top end 130 that permit insertion of the unwound wire and catheter 92 into the oval channel 128.

The U-shaped rail 121 may be formed in a 180 degree arch such that the insertion of the unwound wire and catheter 92 into one end of the U-shaped rail 121 will divert the direction of the unwound wire and catheter 92 by 180 degrees. It is understood that the U-shaped rail 121 may also be formed of an arch that is less than or greater than 180 degrees to divert the direction of the unwound wire and catheter 92 by less than or greater than 180 degrees as desired. For example, in an alternative embodiment, the U-shaped rail 121 may be formed as a circle segment that is 90 degrees such that the insertion of the unwound wire and catheter 92 into one end of the U-shaped rail 121 will divert the direction of the unwound wire and catheter 92 by 90 degrees.

Referring now to FIG. 11, the present invention may further include a wire and catheter guard rail 140 that may be used to clip and retain unwound wires and catheters 92, for example, to keep the wire and catheter off the ground and extending along the operating or surgical table in a desired orientation during surgery.

The wire and catheter guard rail 140 may be comprised of a rectangular plate 142 having a length and a height, where the length of the rectangular plate 142 is greater than the height of the rectangular plate 142. The length of the rectangular plate 142 may be at least 30 cm and at least 40 cm and at least 50 cm and the height of the rectangular plate 142 may be approximately 3 cm to 10 cm.

An upper end of the rectangular plate 142 may support a pair of upwardly extending hooks 144 having shanks 146 extending upwardly at upper, outer ends of the rectangular plate 142 and bending forwardly in a direction perpendicular to a plane of the rectangular plate 142 to a point 148 of the hook 144. The bend of the hook 144 may have an opening width between the shank 146 and the point 148 that is wide enough to catch wires and catheters from falling off the operating or surgical table.

The upper, outer ends of the rectangular plate 142 may further support a pair of wire clips 150 providing C-shaped channels allowing the unwound wire and catheter 92 to be inserted through the wire clips 150 and held along the rectangular plate 142.

The rectangular plate 142 may extend along and be secured to the operating or surgical table with the wire clips 150 resting upon an upper surface of the table. Unwound wire and catheter 92 may be secured along the upper surface of the table within the wire clips 150 while the pair of upwardly extending hooks 144 may act as a guard rail to catch any wire and catheter 92 which gets loose from the wire clips 150 and prevent the wire and catheter 92 from falling off the table.

It is understood that the disk organizer 91, wire and catheter diverter 120, and the wire and catheter guard rail 140 may sold as part of kit along with the disk holder 10 to provide a set of devices that may be used for wire and catheter management during surgery.

References to "wire and catheter" and "wires and catheters" made in this application may refer to either or both the wire and catheter which may be retained within the disk holder 10.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What I claim is:

1. A guidewire and catheter holder for retaining coiled guidewire and catheters comprising:
   a disk extending along a plane and having an upper surface;
   vertically extending sidewalls attached at a periphery of the disk and providing an inwardly concave channel, the disk and vertically extending sidewalls adapted to allow a coiled guidewire and catheter to slide along the upper surface of the disk and come into contact with the vertically extending sidewalls to be received by the inwardly concave channel;
   an axle extending upwardly from a central portion of the upper surface of the disk; and
   at least one cutout in the vertically extending sidewalls defined by opposed vertically extending edges of the vertically extending sidewalls on either side of the at least one cutout and allowing insertion or extraction of the coiled guidewire and catheter through the at least one cutout in the vertically extending sidewalls along the plane of the disk;
   wherein the at least one cutout subtends an angle of at least 30 degrees along the plane of the disk and about the center of the disk and wherein the opposed vertically extending edges of the at least one cutout are separated by at least 7 cm,
   a spool sized to be inserted into the disk and rotated with respect to the disk wherein the spool is configured to retain an end of the coiled guidewire and catheters.

2. The guidewire and catheter holder of claim 1 further including at least one second cutout through the disk aligned with the at least one cutout.

3. The guidewire and catheter holder of claim 2 wherein the at least one second cutout has a width at the periphery of the disk configured to receive a first of an average human adult.

4. The guidewire and catheter holder of claim 2 wherein the vertically extending sidewalls overhang the at least one second cutout by at least 1 cm.

5. The guidewire and catheter holder of claim 2 further comprising overhanging rims extending from outer edges of the at least one second cutout and adapted to assist with retaining the guidewires and catheters as they are being inserted into the disk.

6. The guidewire and catheter holder of claim 5 wherein the axle includes a central, vertically extending bore.

7. The guidewire and catheter holder of claim 5 wherein the axle has a cylindrical outer surface.

8. The guidewire and catheter holder of claim 1 wherein the disk is a circle that has a diameter that is greater than 10 cm and less than 50 cm.

9. The guidewire and catheter holder of claim 1 wherein the spool is configured to retain an end of the coiled guidewire or catheters within a pair of perpendicularly extending slits of the spool.

10. The guidewire and catheter holder of claim 1 wherein the spool is configured to retain an end of the coiled guidewire or catheters at an angle wherein the coiled guidewire or catheters are configured to extend from the spool at an angle that is not tangent to an outer perimeter of the spool.

11. The guidewire and catheter holder of claim 1 wherein the disk supports at least one drainage hole permitting fluid to flow between the upper surface of the disk and a lower surface of the disk.

12. A method of retaining coiled guidewire and catheters, the method comprising the steps of:
   providing a guidewire and catheter holder having a disk extending along a plane and having an upper surface, and vertically extending sidewalls attached at a periphery of the disk providing an inwardly concave channel, the disk and vertically extending sidewalls adapted to allow a coiled guidewire and catheter to slide along the upper surface of the disk and come into contact with the vertically extending sidewalls to be received by the inwardly concave channel; and an axle extending upwardly from a central portion of the upper surface of the disk; and at least one cutout in the vertically extending sidewalls defined by opposed vertically extending edges of the vertically extending sidewalls on either side of the at least one cutout and allowing insertion or extraction of the coiled guidewire and catheter through the vertically extending sidewalls along a plane of the disk; wherein the at least one cutout subtends an angle of at least 30 degrees along the plane of the disk and about the center of the disk and wherein the opposed vertically extending edges of the at least one cutout are separated by least 7 cm, and a spool sized to be inserted into the disk and rotated with respect to the disk wherein the spool is configured to retain an end of the coiled guidewire and catheters;

sliding a coiled guidewire or catheter through the at least one cutout along the plane of the disk; and releasing the coiled guidewire or catheter so that the inwardly concave channel receives the coiled guidewire or catheters expanding into contact with the vertically extending sidewalls.

\* \* \* \* \*